US010251656B2

United States Patent
Granberry et al.

(10) Patent No.: US 10,251,656 B2
(45) Date of Patent: Apr. 9, 2019

(54) DRILL/DRIVER HYBRID INSTRUMENT FOR INTERPHALANGEAL FUSION

(71) Applicant: ARTHREX, INC., Naples, FL (US)

(72) Inventors: William M. Granberry, Houston, TX (US); Stephanie A. Bare, Naples, FL (US); Chris M. Powell, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 15/606,336

(22) Filed: May 26, 2017

(65) Prior Publication Data

US 2017/0265875 A1 Sep. 21, 2017

Related U.S. Application Data

(63) Continuation of application No. 14/206,885, filed on Mar. 12, 2014, now Pat. No. 9,687,256.

(60) Provisional application No. 61/778,513, filed on Mar. 13, 2013.

(51) Int. Cl.
| | |
|---|---|
| *A61B 17/16* | (2006.01) |
| *A61B 17/72* | (2006.01) |
| *A61B 17/86* | (2006.01) |
| *B25F 3/00* | (2006.01) |
| *E21B 10/42* | (2006.01) |

(52) U.S. Cl.
CPC ...... *A61B 17/1682* (2013.01); *A61B 17/7291* (2013.01); *A61B 17/863* (2013.01); *B25F 3/00* (2013.01); *E21B 10/42* (2013.01)

(58) Field of Classification Search
CPC .......... B25F 3/00; E21B 10/42; A61B 17/1615
See application file for complete search history.

(56) References Cited

U.S. PATENT DOCUMENTS

| | | | |
|---|---|---|---|
| 4,723,541 A * | 2/1988 | Reese | A61B 17/72 606/316 |
| 5,417,692 A | 5/1995 | Goble et al. | |
| 5,975,815 A * | 11/1999 | Zierpka | B25B 21/007 279/22 |
| 6,312,432 B1 * | 11/2001 | Leppelmeier | A61B 17/1615 408/225 |
| 7,041,106 B1 | 5/2006 | Carver et al. | |
| 8,070,786 B2 | 12/2011 | Huebner et al. | |
| 8,529,611 B2 | 9/2013 | Champagne et al. | |
| 8,608,785 B2 | 12/2013 | Reed et al. | |
| 2010/0036439 A1 | 2/2010 | Lavi | |
| 2011/0054545 A1 | 3/2011 | Champagne et al. | |

(Continued)

*Primary Examiner* — Andrew Yang
(74) *Attorney, Agent, or Firm* — Carlson, Gaskey & Olds, P.C.

(57) ABSTRACT

Surgical techniques, instruments and systems for bone fusions and repairs (for example, phalangeal fusion) which allow alignment of small bones (for example, phalanges) without the use of guidewire and cannulated instrumentation such as, for example, drills and drivers, and cannulated screws. A drill/driver hybrid instrument (a combined drill/driver device) may be used in fusion of two small bones (for example, in interphalangeal fusion). One end of the hybrid instrument is provided with a plurality of flutes so that the instrument can be used as a drill to remove bone. The other end is shaped to mate with a device to be inserted intraarticularly (for example, interphalangeally), acting as a driver for that device.

20 Claims, 6 Drawing Sheets

(56) References Cited

U.S. PATENT DOCUMENTS

2011/0276099 A1    11/2011  Champagne et al.
2011/0301653 A1*   12/2011  Reed .................. A61B 17/1604
                                                           606/319
2012/0065692 A1    3/2012   Champagne et al.

* cited by examiner

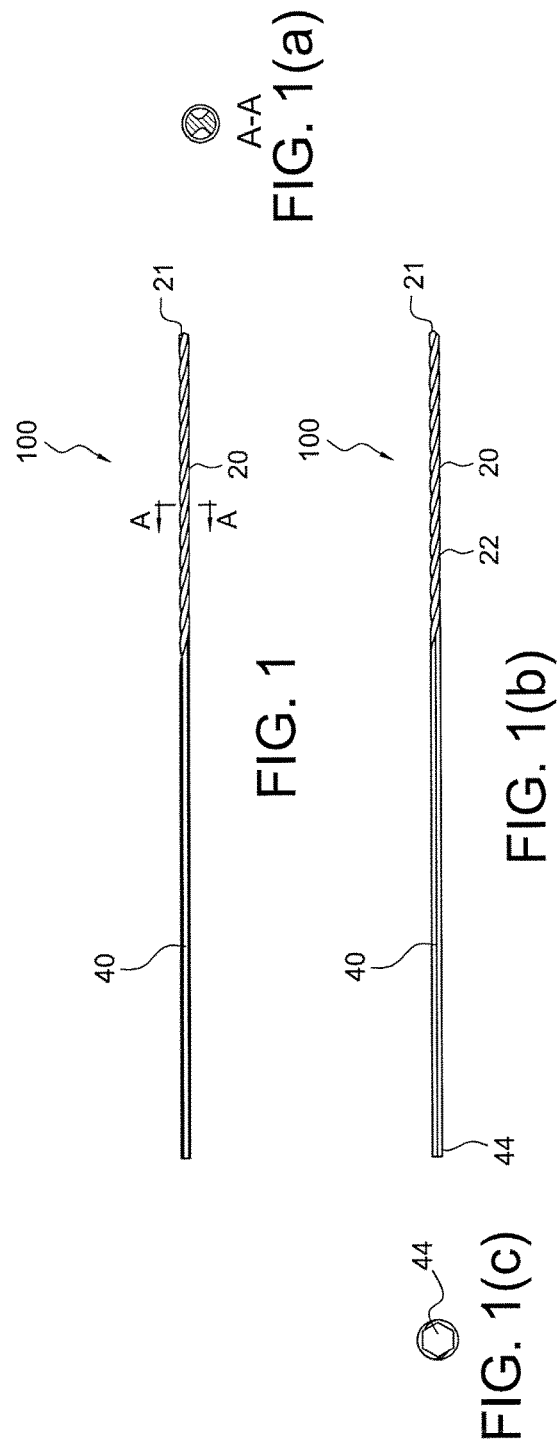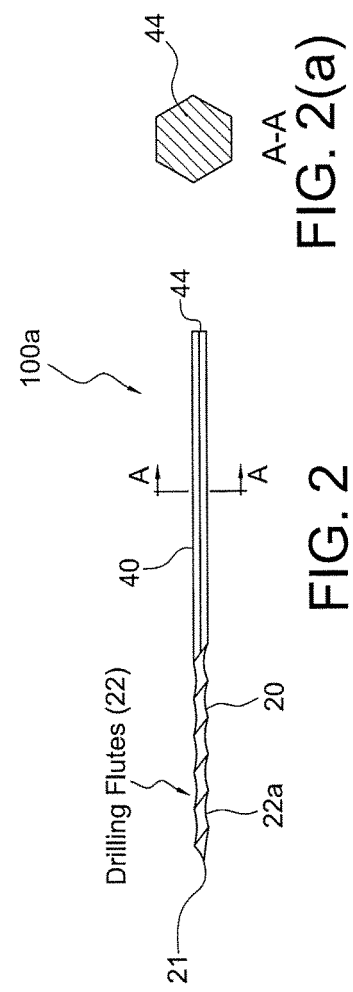

Resected ends of proximal and distal phalanges

DRILL/DRIVER HYBRID INSTRUMENT FOR INTERPHALANGEAL FUSION

CROSS-REFERENCE TO RELATED APPLICATIONS

This application is a continuation of U.S. patent application Ser. No. 14/206,885, filed Mar. 12, 2014, which claims the benefit of U.S. Provisional Application No. 61/778,513, filed Mar. 13, 2013, the disclosures of which are incorporated by reference in their entirety herein.

FIELD OF THE INVENTION

The present invention relates to the field of surgery and, more particularly, to improved instruments, systems and methods for small joint repairs (hand, wrist and foot repairs, for example) and ligament reconstructions.

BACKGROUND OF THE INVENTION

Phalanges of the hand are known as finger bones. Phalanges of the foot are known as toe bones. The metacarpals are tiny long bones in the hand that connect the phalanges to the carpals. The metatarsals are short bones in the foot that connects the phalanges to the tarsals.

Interphalangeal joints are the joints between the phalanges. These small joints are typically classified as "proximal interphalangeal joints" (PIP or PIPJ, or joints between the first (proximal) and second (intermediate) phalanges) or "distal interphalangeal joints" (DIP or DIPJ, or joints between the second and third (distal) phalanges).

Abnormalities associated with disruptions of these small joints (such as PIP or DIP joints) are caused by biomechanical abnormalities (for example, where certain tendons, ligaments, and supportive structures of the joint are no longer functioning correctly) or other various injuries (for example, sport injuries).

The PIP joint is a hinge joint that is normally kept in alignment by a soft tissue envelope consisting of joint capsule, the volar plate, collateral ligaments and the central slip. These structures form a tight-fitting "box" with a very narrow joint space. When injuries to this soft tissue envelope occur, they can be either partial or complete and they cause disruption to the collateral ligaments and adjacent structures.

Similarly, when the first metatarsophalangeal joint (MTP) (which is one of the joints in the big toe) is affected by arthritis, for example (such as Hallux Rigidus), the cartilage of the joint becomes damaged which in turn can cause extreme pain and stiffness. To alleviate pain, a fusion operation (arthrodesis) is recommended to totally remove the damaged cartilage and to fuse the two bones that form the joint. The fusion is usually secured by either two fixation devices (for example, screws) or a plate that remain in toe permanently.

There is a need for a small joint repair technique that is simple and is performed by a minimally invasive "all-inside" approach. Also needed is a novel instrument that allows both removal of bone from a small bone (for example, phalanx) and also insertion of a fixation device (for example, implant) into the bone.

SUMMARY OF THE INVENTION

The present invention provides surgical techniques, instruments and systems for bone fusions and repairs (for example, phalangeal fusion) which allow alignment of small bones (for example, phalanges) without the use of guidewire and cannulated instrumentation such as, for example, drills and drivers, and cannulated screws.

The present invention provides a drill/driver hybrid instrument (a combined drill/driver pin) that may be used in fusion of two small bones (for example, in interphalangeal fusion). One end of the hybrid instrument is provided with a plurality of flutes or threads so that the instrument can be used as a drill to remove bone. The other end is shaped to mate with a device to be inserted intraarticularly (for example, interphalangeally), acting as a driver for that device.

The present invention also provides fusion methods for small bones by a minimally invasive all-inside approach. The method comprises the steps of: (i) providing a single-shaft drill/driver hybrid instrument in the vicinity of a small bone joint; (ii) forming a bone tunnel/socket with one end of the hybrid instrument; and (iii) engaging/inserting a device (for example, a fixation device such as screw repair implant) with the another end of the instrument.

These and other features and advantages of the present invention will become apparent from the following description of the invention that is provided in connection with the accompanying drawings and illustrated embodiments of the invention.

BRIEF DESCRIPTION OF THE DRAWINGS

FIG. 1 illustrates a front view of a drill/driver hybrid instrument according to an exemplary embodiment of the present invention.

FIG. 1(a) illustrates a cross-sectional view of the drill/driver hybrid instrument of FIG. 1, taken along line A-A of FIG. 1.

FIG. 1(b) illustrates another front view of the drill/driver hybrid instrument of FIG. 1.

FIG. 1(c) illustrates a left-side view of the drill/driver hybrid instrument of FIG. 1.

FIG. 2 illustrates a front view of a drill/driver hybrid instrument according to another exemplary embodiment of the present invention.

FIG. 2(a) illustrates a cross-sectional view of the drill/driver hybrid instrument of FIG. 2, taken along line A-A of FIG. 2.

DETAILED DESCRIPTION OF THE PREFERRED EMBODIMENTS

Figure 3:
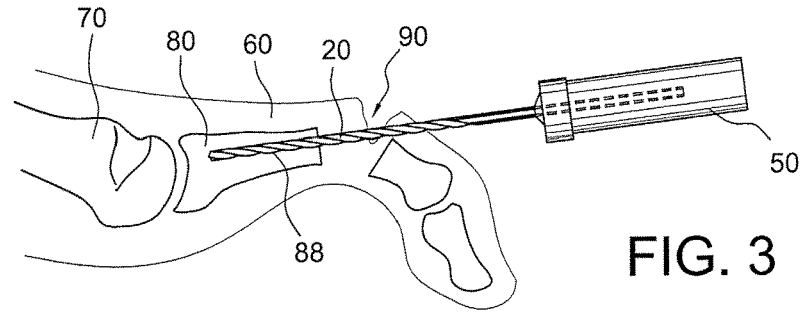
FIGS. 3-6 illustrate subsequent steps of an exemplary method of phalangeal fusion with the drill/driver hybrid instrument of FIG. 1.

The present invention provides methods and apparatus for small bone repairs and fusion, with particular application to phalangeal repairs and fusions.

The present invention provides surgical procedures, instruments and systems for bone fusion and repair (for example, phalangeal fusion) which allow alignment of small bones (for example, phalanges) without the use of guidewire and cannulated instrumentation, e.g., screws.

An exemplary instrument of the present invention is a drill/driver hybrid instrument (a combined device) in the form of a solid rigid pin that may be used in small bone repairs, for example, interphalangeal fusion. The hybrid instrument is provided with first and second ends. One of the first and second ends (the "drill" end) has a plurality of flutes/threads so that the instrument can be used as a drill to remove material from bone (phalangeal canals). The other of the first and second ends (the opposite end or the "driver" end) is shaped to engage/mate with a device to be inserted intraarticularly (e.g., interphalangeally) and acts as a driver for that device. The "driver" end could have any suitable cross-section, for example, hexagonal, hexalobe, cruciform, a "star" like configuration, or any other shape and geometry that allows the end to mate with an implanted device in the joint.

Another exemplary device of the present invention (which could be used with the methods of fusion and small bone repairs) is a fixation device in the form of a small screw with two separate threads on a shaft. The shaft may be selected to have a diameter corresponding to the size of the bones to be fused/repaired. In an exemplary embodiment, the diameter of the shaft may be of about 1.5 mm to about 4.5 mm, preferably about 2 mm or less. For metatarsals or other bones, however, the diameter may be larger than 2 mm. The threads have different directions and are provided at a proximal end and at a distal end, respectively, of the shaft of the fixation device. The threads are opposing so that, during insertion, the small screw can be turned clockwise to allow for simultaneous and opposite engagement of both phalanges (bone fragments). This allows for appropriate placement of the screw and toe prior to compression.

Referring now to the drawings, where like elements are designated by like reference numerals, FIGS. 1-6 illustrate exemplary embodiments of drill/driver hybrid instrument/pin 100, 100a of the present invention and methods of bone fusion and repair employing such instrument/pin 100, 100a. FIGS. 7-13 illustrate exemplary embodiments of a solid fixation device 195 (an exemplary retro compression solid screw) and exemplary methods of implanting the solid fixation device according to the present invention.

In the embodiments below, instrument/pin 100, 100a and fixation device 195 are described with reference to a particular interphalangeal repair (fusion) in the foot. The invention is not limited, however, to this specific exemplary embodiment and encompasses hybrid instruments and accompanying fixation devices with application to any other small joint repairs and any other interosseous ligament reconstructions, for example, MTP and MCP joint repairs, syndesmotic injuries and hallux valgus repairs, among many others. Thus, the instruments and methods of the present invention have applicability to the repair and/or fusion of any adjacent bones, for example, adjacent phalanges, metatarsals, metacarpals, tarsals or carpal bones.

Hybrid instrument 100, 100a of FIGS. 1-2(a) is provided with a first end 20 (drill end 20) and a second end 40 (opposite end 40 or driver end 40). In an exemplary embodiment, first end 20 of pin 100 (FIG. 1) is provided with a sharp tip 21 and a plurality of threads 22 configured to remove bone (drill) and form a bone socket/tunnel, as detailed below. In another exemplary embodiment, first end 20 of pin 100a (FIG. 2) is provided with a sharp tip 21 and a plurality of drilling flutes 22a configured to remove bone (drill) and form a bone socket/tunnel, as detailed below.

Second end 40 is provided with an end geometry 44 configured to engage (mate with) a device (for example, a fixation device such as a screw) to be inserted intraarticularly (for example, interphalangeally). The second end 40 acts as a driver for that device (fixation device). The second end 40 (driver end 40) could have any suitable cross-section, for example, hexagonal, hexalobe, cruciform, a "star" like configuration, or any other shape and geometry that allows the end to mate with a device to be implanted into the joint (for example, interphalangeal joint). FIGS. 1(c) and 2(a) show the second end 40 having an exemplary hexagonal cross-section.

Drill/driver instrument 100, 100a is designed to be used both for drilling bone and for engaging a fixation device to be inserted into the bone by an "all-inside," minimally invasive approach and with minimal trauma to the patient. The instrument/pin 100, 100a may be provided with markings to aid in assessing the drill and/or insertion depth. The diameter of instrument/pin 100, 100a may be about 1.0 mm to about 4.5 mm, more preferably about 1.5 mm to about 2.0 mm.

FIGS. 3-6 illustrate an exemplary method of interphalangeal joint repair (phalangeal fusion) with exemplary instrument 100 of FIG. 1.

FIG. 3: Hybrid instrument/pin 100 of the present invention is used to drill into proximal phalanx 80 of interphalangeal joint 90 with first end 20 (drill end) of the instrument. Metatarsal 70 is illustrated as part of toe 60. To facilitate drilling of the instrument 100 into phalanx 80 to form phalangeal canal 88 (bone tunnel or socket 88), a handle 50 may be securely attached to end 40 of the instrument. Phalangeal canal 88 of proximal phalanx 80 is formed by drill threads/flutes 22 (which may be hand drilled or operated under power). Handle 50 attaches to the driver end 40 to allow the application of torque to the drill threads/flutes 22.

Figure 4:
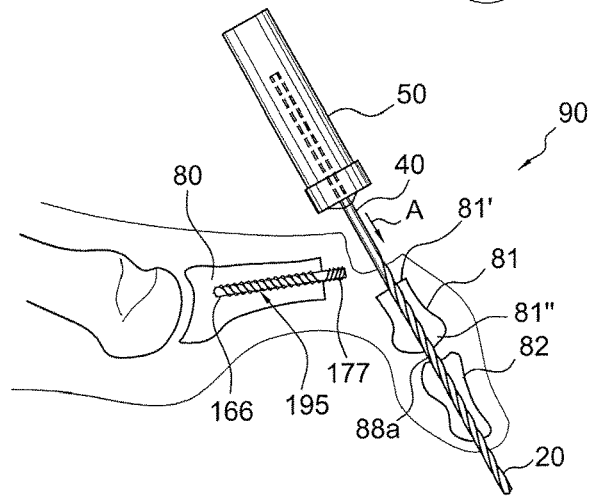

FIG. 4: The drill end 20 of hybrid instrument/pin 100 is removed from the proximal phalanx 80 and then used in middle and distal phalanges 81, 82 to create a tunnel 88a through the tip of the toe 60 (i.e., drilling in the direction of arrow A, from a first surface 81' of distal phalanx 81 to a second surface 81" of the distal phalanx 81). This procedure could be also done with the drill coming out before the end of the toe, i.e., out of the dorsal aspect, just proximal to the DIPJ. This would allow for a flexed fusion which is preferred by some surgeons.

Figure 7A:
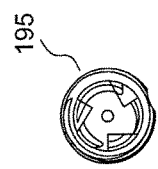
FIG. 7(a) illustrates a right-side view of the internal fixation device of FIG. 7.
Figure 7:
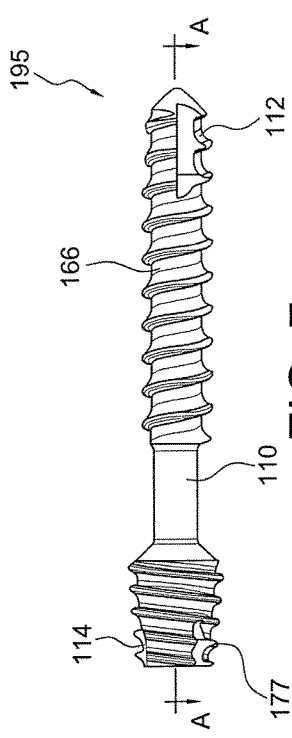
FIG. 7 illustrates a front view of an internal fixation device (a solid rigid screw) according to an exemplary embodiment of the present invention.
Figure 7C:
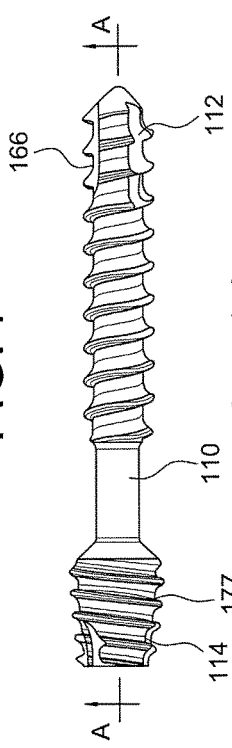
FIG. 7(c) illustrates another view of the internal fixation device of FIG. 7 rotated about 90 degrees.
Figure 7D:
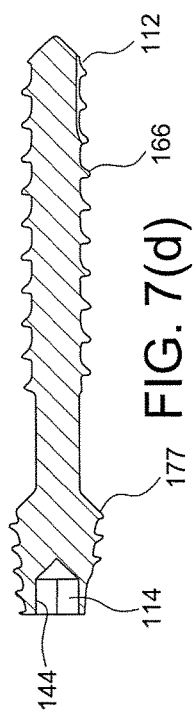
FIG. 7(d) illustrates a cross-sectional view of the internal fixation device of FIG. 7 taken along line A-A of FIG. 7.
Figure 7B:
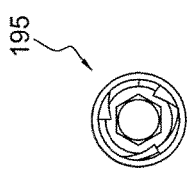
FIG. 7(b) illustrates a left-side view of the internal fixation device of FIG. 7.

Also shown in FIG. 4 is internal fixation device 195 (implant 195 or retro compression screw 195) that will mate later with end 40 of the hybrid instrument/pin 100 (through a socket or opening provided at the distal end of fixation device 195 and configured to engage and mate with the end 40, as detailed below). Implant 195 is shown partially inserted within bone tunnel or socket 88; however, implant 195 may be also provided fully inserted in bone tunnel or socket 88 (i.e., first set of threads 166 may be partially or fully inserted/threaded within bone tunnel or socket 88). Details of implant 195 are illustrated in FIGS. 7-7(d). Depending on the particular application, the outer diameter of the fixation device 195 is slightly larger than the diameter of the respective bone tunnel or socket to be threaded therein, to allow the threads of the shaft of the fixation device 195 to adhere to the internal walls of the bone tunnel or socket.

Figure 5:
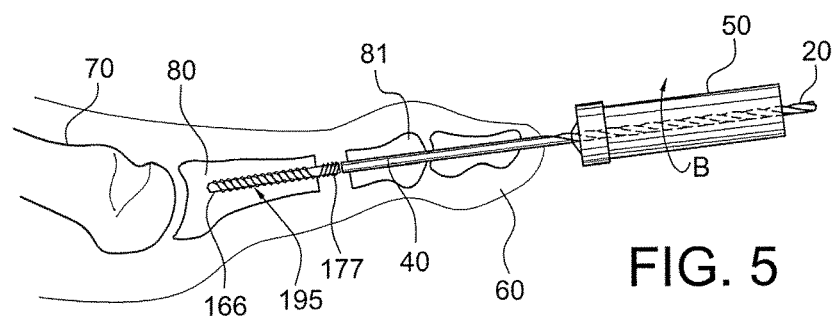

FIG. 5: The handle 50 can then be removed from the interphalangeal area 90 and reattached outside of the toe 60 (i.e., attached to the first end 20). The driver end 40 remains within the phalanx 81 near surface 81' to engage fixation device 195 (implant 195) and drive this device into bone tunnel 88 of proximal phalanx 80 and also into bone tunnel 81*a* of middle phalanx 81. As the handle 50 is rotated in a clockwise direction B, the fixation device 195 is advanced in a first direction (for example, in a forward direction) in bone 80 as threads 166 advance within the bone tunnel 88, and also in a second direction which is opposite the first direction (for example, in a backwards direction) in bone 81 as threads 177 advance within the bone tunnel 88*a*. The fusion of the bones 80, 81 is a result of the opposing threads 166, 177 of the fixation device 195, as detailed below. In this manner, one end of the rigid fixation device 195 is threaded within a first bone tunnel (i.e., bone tunnel 88) and the other end of the rigid fixation device 195 is threaded within a second bone tunnel (i.e., bone tunnel 88*a*) to align the two bone tunnels 88, 88*a* and the two bones 80, 81. If the fixation device 195 is fully seated (fully threaded) within the bone tunnel or socket 88, then rotation of the handle 50 in the direction of arrow B allows threading of the fixation device 195 only in the bone tunnel or socket 88*a* to allow the two bones 80, 81 to be brought together and fuse.

Figure 6:
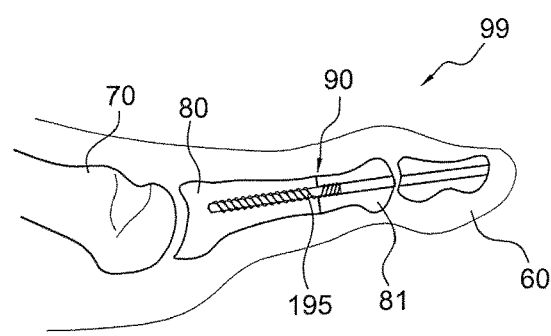

FIG. 6: The device 100 can then be removed from the distal end of the toe 60 and the implant 195 of repair 99 is left in the joint 90 (for example, interphalangeal joint 90).

The drill/driver hybrid device/pin 100, 100*a* of the present invention could be used for implantation in the proximal interphalangeal joint (PIP) or distal interphalangeal joint (DIP) of the hands and/or feet. Device 100, 100*a* could also be used at the metatarsal-phalangeal (MTP) or metacarpal-phalangeal (MCP) joints.

Device/pin 100, 100*a* could benefit an "all-inside" implant that fuses/reconstructs/repairs/spans the joint and is inserted from within the joint. The device/pin 100, 100*a* is used for drilling bone and also engaging an implant (fixation device such as a screw, for example).

The reconstruction system and procedure detailed above offer a minimally invasive approach. The single-shaft hybrid instrument 100, 100*a* with drill end 20 and driver end 40 allows both the formation of a bone tunnel (phalangeal tunnel) and also the insertion of a screw repair implant, with minimal trauma to the patient.

FIGS. 7-7(*d*) illustrate another exemplary embodiment of fixation device 195 (retro compression screw 195) of the present invention. Fixation device 195 is preferably solid (non-cannulated) and rigid to allow implantation into bone without the need for cannulated fixation devices and associated instrumentation.

Fixation device 195 is an exemplary small screw with two separated threads 166, 177 provided on a shaft 110 which may have any diameter corresponding to the particular bone application, for example, about 4.5 mm or less, preferably 2.0 mm or less, depending on the bones to be fused and/or the particular application (i.e., larger bones would require larger diameter screws). Proximal threads 166 are provided at a proximal end 112 of the shaft 110. Distal threads 177 are provided at a distal end 114 of the shaft 110. The proximal and distal threads 166, 177 have opposite threads to allow for compression of the two bones with clockwise revolutions. Fixation device 195 may have any length depending on the particular bone application/repair. In an exemplary only embodiment, the screw 195 could be from about 12 mm to about 40 mm in length, preferably about 20 mm to about 40 mm in length. The threads within the proximal phalanx are long and the threads within the middle phalanx can be wider (i.e., similar to a Herbert screw). Distal end 114 is also provided with a socket or opening 144 that is configured to engage and mate with the end 40 of hybrid instrument 100, and as detailed below.

The novelty of the device 195 consists in the opposing threads 166, 177 on the shaft and in the insertion technique. The threads 166, 177 are opposing so that, during insertion, the screw can be turned clockwise to allow for simultaneous and opposite engagement of both phalanges. This allows for appropriate placement of the screw 195 and toe prior to compression.

Exemplary internal fixation device 195 of FIG. 7 may be also employed for fixation of hammertoes during reconstruction, or for other fixations/repairs. Fixation device 195 is rigid, provides compression and is easily implanted, similar to the standard technique of pin fixation, as shown with reference to FIGS. 8-13.

Hammertoe surgery is a very common procedure which is typically performed with resection of the proximal interphalangeal joint (PIP or PIPJ). The most common known fixation technique utilizes a smooth k-wire that is later removed. A bioabsorbable pin may be also employed, but this pin is typically too weak and does not provide compression. In addition, when fusion of the joint is required, unfavorable results may occur, generally related to deformity and delayed union causing prolonged swelling.

Internal fixation is also accompanied by problems. The device must be placed into the PIPJ without damage to the DIPJ. During the resection of the joint, only the PIP is exposed. The bones are quite small, especially the middle phalanx 81 which has a length between 5 mm to 20 mm. The diameter of the proximal phalanx 80 is also small and averages approximately 2 mm. Longitudinal alignment during insertion of the device is difficult to maintain.

Fixation device 195 of the present invention overcomes the above problems. By being provided with two separate and different threads on a small shaft, fixation device 195 can be turned clockwise to allow for simultaneous and opposite engagement of both phalanges (due to the opposing threads). This allows for appropriate placement of the screw and toe prior to compression.

The insertion technique with fixation device 195 is designed to mimic typical articular joint (for example, PIPJ) fixation with a smooth pin. First, a smooth pin of about 1.5 to 2.0 mm diameter is driven prograde (antegrade) or distally out the end of the toe (similarly to the standard technique). This pin has one sharp end and the other end has a small hexagonal shaped tip that fits into the screw. The pin is also marked for measurement purposes. An exemplary pin is instrument 100, 100*a* of FIGS. 1 and 2.

Once the pin position is acceptable, the screw 195 is started retrograde into the proximal phalanx 80. When it is inserted to within a few millimeters of the distal threads 177, it is placed onto the hex driver end 44 of the pin 100 in the distal part of the toe 60. Then, as the pin 100 is turned clockwise using the pin protruding out the tip of the toe, the two bone fragments 80, 81 are drawn together. The pin is then removed from the toe leaving only the screw 195 across the articular joint, for example, DIPJ or PIPJ joint.

The desirable lengths and the markings on the insertion pin 100 required for sizing the pin may be calculated appropriately. Another benefit of the design of fixation device 195 is that the threads engaging the middle phalanx can be large without damaging the DIPJ. The only special tools that are required beyond a wire driver are a small screwdriver and a hand-held chuck to rotate the pin 100.

Figure 8:
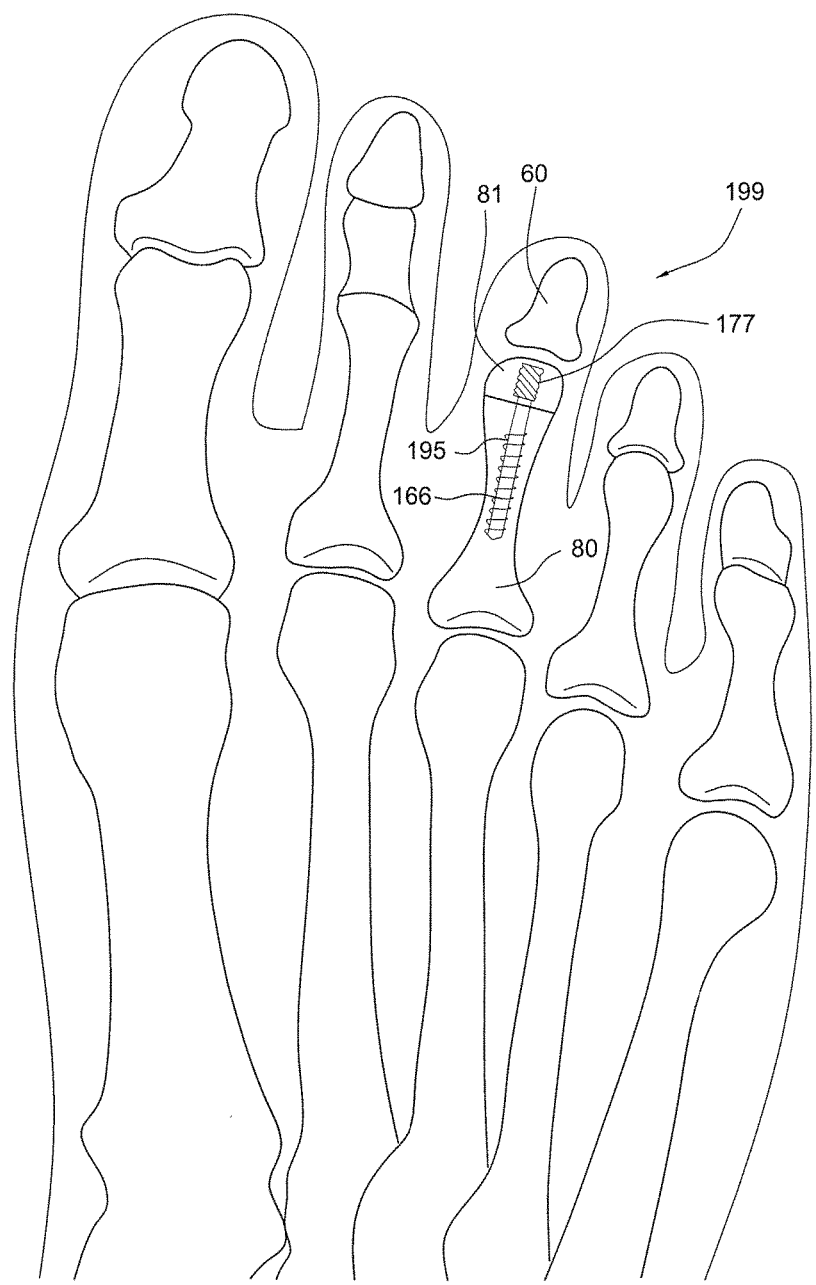
FIG. 8 illustrates an X-ray of the foot showing the head of the internal fixation device of FIG. 7 fully seated in the middle phalanx.

FIG. 8 illustrates an X-ray of the foot showing the head of the internal fixation device 195 of FIG. 7 fully seated in the middle phalanx 81 of toe 60 as part of fusion repair 199.

FIGS. 9-13 illustrate subsequent steps of an exemplary method of phalangeal repair with the internal fixation device 195 of FIG. 7.

Figure 9:
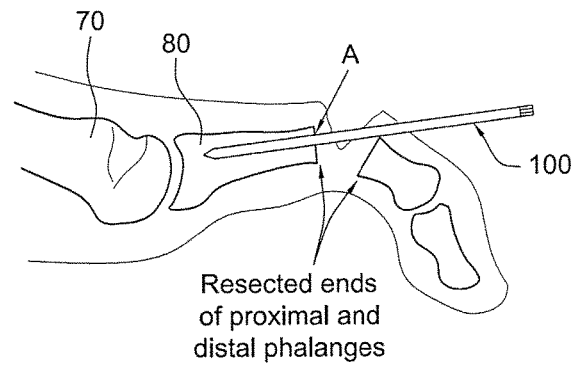
FIGS. 9-13 illustrate subsequent steps of an exemplary method of phalangeal fusion with the internal fixation device of FIG. 7.

FIG. 9: Step 1—Retrograde cannulation of proximal phalanx 80 adjacent metatarsal 70 with hybrid instrument/pin 100; make note of length "A." FIG. 9 also shows the resected ends of the proximal and distal phalanges.

Figure 10:
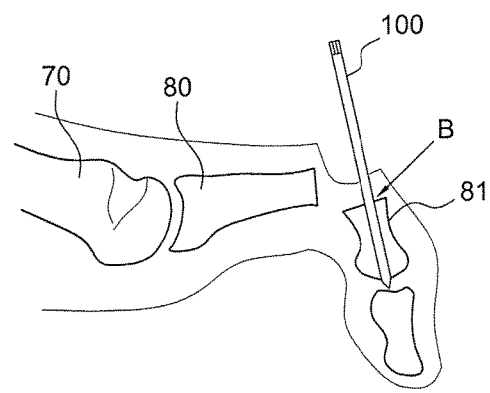

FIG. 10: Step 2—Cannulate toe tip; same pin (for example, instrument 100) is driven prograde out of toe tip; two measurements are taken; "B" represents the depth until PIPJ is fixed; pin 100 is inserted when DIPJ has crepitus; take measurement—this is the length of the middle phalanx 81.

Figure 11:
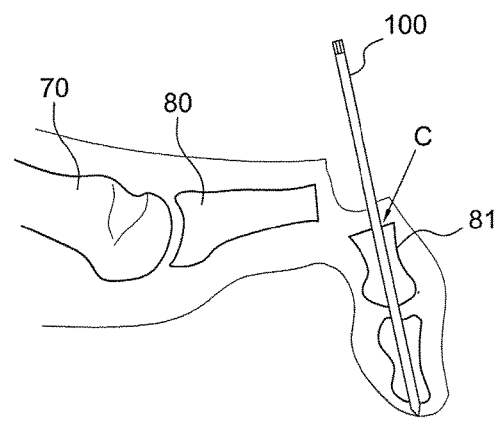

FIG. 11: The pin 100 is driven to just under the skin at the toe tip; take third measurement "C." This provides final insertion length "D" (C-B=D);

Step 3—Pin 100 driven until flush with middle phalanx 81.

Figure 12:
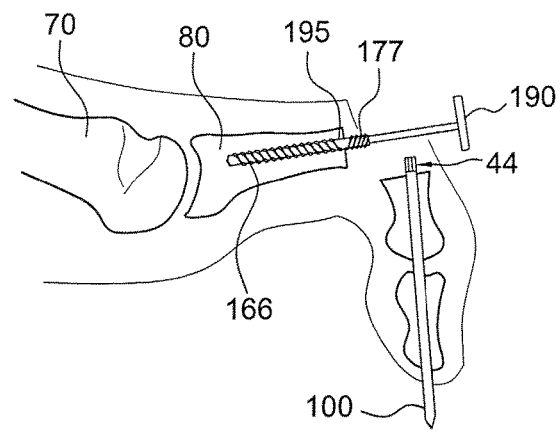

FIG. 12: step 4—Screw 195 inserted retrograde into proximal phalanx 80 with a small insertion driver 190; screw 195 is inserted until few mm of the shaft are still visible; only the hex drive 44 of the pin 100 is visible (insertion pin 100 remains in place).

Step 5—Straighten the toe and engage hex end 44 of pin 100 in socket 144 of screw 195; this may be difficult as there is limited space in the dissection between the bones (typically 10-15 mm distraction is possible).

Figure 13:
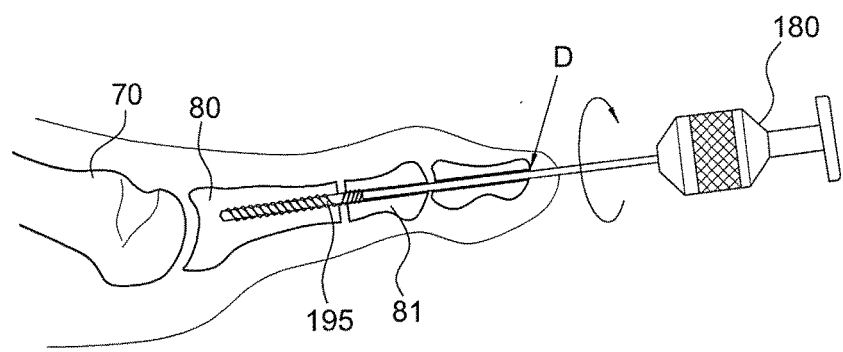

FIG. 13: Step 6—rotate the insertion pin 100 (with screwdriver 180) in a clockwise manner to compress the bones 80, 81; as the pin 100 is turned, care should be taken to ensure that the threads in the middle phalanx engage; as the bones 80, 81 compress and the threads work into the proximal phalanx, complete insertion is monitored by 1) visualizing the bone and 2) observing the measurement on the pin 100 (should be equal to or just less than "D" from above).

Implant (fixation device) 195 described above may be an exemplary hammertoe screw employed, for example, in a metatarsal osteotomy for bunionectomy. Implant 195 may be part of a kit (set) for metatarsal osteotomy, or may be provided separately, in various lengths and/or diameters. As noted, implant 195 is solid to allow implantation/fixation into bone without the need for cannulated implants and instruments. In particular applications, however, the invention also contemplates a fixation device that is partially cannulated (or even fully cannulated).

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents falling within the scope of the invention. Accordingly, the invention is to be limited not by the specific disclosure herein, but only by the appended claims.

What is claimed is:

1. A surgical system, comprising:
  a fixation device including a first thread and a second thread, wherein the first thread and the second thread are opposing threads, and the first thread is longer than the second thread; and
  a hybrid drill/driver instrument including:
    a pin extending between a driver end and a drill end, and
    a handle movable between a first position in which it is secured to the driver end of the pin and a second position in which it is secured to the drill end of the pin, wherein the handle includes a cannulation for receiving either the driver end or the drill end of the pin.

2. The surgical system as recited in claim 1, wherein the driver end of the pin includes an end geometry configured to engage a socket of the fixation device.

3. The surgical system as recited in claim 2, wherein the end geometry includes a hexagonal cross-sectional shape.

4. The surgical system as recited in claim 1, wherein the drill end of the pin terminates in a sharp tip.

5. The surgical system as recited in claim 1, wherein the pin includes a diameter of about 1.0 mm to about 4.5 mm.

6. The surgical system as recited in claim 1, wherein the pin includes a diameter of about 1.5 mm to about 2.0 mm.

7. The surgical system as recited in claim 1, wherein the pin includes a plurality of markings for accessing a depth of the pin in bone.

8. The surgical system as recited in claim 1, wherein the pin is solid and rigid.

9. The bone fusion system as recited in claim 1, wherein the drill end of the pin includes a plurality of drill flutes or threads adapted to drill bone.

10. The surgical system as recited in claim 1, wherein the first thread is a proximal thread and the second thread is a distal thread.

11. The surgical system as recited in claim 1, wherein the second thread is wider than the first thread.

12. A surgical system, comprising:
  a fixation device including a first thread and a second thread, wherein the first thread and the second thread are opposing threads, and the first thread is longer than the second thread; and
  a hybrid drill/driver instrument including:
    a pin longitudinally extending between a driver end that includes an end geometry configured to engage the fixation device and a drill end that includes drilling threads and a sharp tip, wherein the pin is solid, and
    a handle removably securable to either the driver end or the drill end of the pin, the handle including a cannulation for receiving either the driver end or the drill end of the pin, wherein the handle is movable between a first position in which it is secured to the driver end of the pin and a second position in which it is secured to the drill end of the pin.

13. The surgical system as recited in claim 12, wherein the first thread is a proximal thread and the second thread is a distal thread.

14. The surgical system as recited in claim 12, wherein the second thread is wider than the first thread.

15. A bone fusion system, comprising:
  a fixation device including a socket, a first thread, and a second thread, wherein the first thread is longer than the second thread; and
  a hybrid drill/driver instrument including a pin longitudinally extending between a driver end adapted to mate with the socket of the fixation device and a drill end adapted to drill a bone hole for inserting the fixation device, wherein the first thread and the second thread of the fixation device are opposing threads.

16. The bone fusion system as recited in claim 15, wherein the fixation device is a non-cannulated compression screw.

17. The bone fusion system as recited in claim 15, wherein the first thread is separated from the second thread along a shaft of the fixation device.

18. The bone fusion system as recited in claim 15, wherein the drill end of the hybrid drill/driver instrument is provided with a plurality of drill flutes or threads.

19. The bone fusion system as recited in claim 15, wherein the first thread is a proximal thread and the second thread is a distal thread.

20. The bone fusion system as recited in claim 15, wherein the second thread is wider than the first thread.

\* \* \* \* \*